(12) United States Patent
Lee et al.

(10) Patent No.: US 7,990,536 B2
(45) Date of Patent: Aug. 2, 2011

(54) SYSTEM AND METHOD FOR MEASURING REFLECTANCE OF OBJECT

(75) Inventors: Kwan Heng Lee, Gwangju (KR); Duck Bong Kim, Gwangju (KR); Kang Su Park, Gwangju (KR); Kang Yeon Kim, Gwangju (KR); Myoung Kook Seo, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 94 days.

(21) Appl. No.: 12/536,292

(22) Filed: Aug. 5, 2009

(65) Prior Publication Data

US 2010/0033721 A1 Feb. 11, 2010

(30) Foreign Application Priority Data

Aug. 7, 2008 (KR) .................. 10-2008-0077467
Jul. 24, 2009 (KR) .................. 10-2009-0068011

(51) Int. Cl.
*G01J 3/52* (2006.01)

(52) U.S. Cl. .................. 356/421; 356/455; 356/237.6
(58) Field of Classification Search .......... 356/421–445, 356/237.1–237.6
See application file for complete search history.

(56) References Cited

U.S. PATENT DOCUMENTS 6,201,892 B1 * 3/2001 Ludlow et al. ............. 356/237.1
7,286,242 B2 * 10/2007 Kim et al. ..................... 356/504

* cited by examiner

*Primary Examiner* — Gregory J Toatley
*Assistant Examiner* — Iyabo S Alli

(57) ABSTRACT

There are disclosed a system and a method for measuring reflectance of an object. The system for measuring reflectance of an object according to the present invention includes: a light source unit including a light source irradiating light to the object; a light source position adjusting unit that adjusts a position and a direction of the light source unit; a light receiving unit that acquires image data by detecting light reflected on the object; and a reflectance acquiring unit that acquires the reflectance of the object from the image data. According to the present invention, it is possible to more precisely acquire the reflectance of the object within a shorter time.

16 Claims, 11 Drawing Sheets

SYSTEM AND METHOD FOR MEASURING REFLECTANCE OF OBJECT

BACKGROUND OF THE INVENTION

1. Field of the Invention

The present invention relates to a computer graphics, and more particularly, to a system and a method for measuring reflectance of an object for modeling a realistic image of an object.

2. Description of the Related Art

A function representing characteristics of the surface of an object by using an incident angle and a reflection angle of light emitted from a light source is referred to as a bi-directional reflectance distribution function (BRDF) at the time of modeling a realistic image of the object. The BRDF is defined as a ratio of incident energy flux and radiance of light reflected on the surface of the object.

Information on reflectance of the object is generally represented by the BRDF. An image of the object can be simulated by calculating reflection energy of the object to the light source by using the reflectance of the object. That is, it is possible to simulate the image of the object generally existing on a circumference, which can be seen in a photograph or seen by a human at a place where the light source is provided.

In general, in order to measure the BRDF of the object, the light sources are disposed at all locations where the light sources can influence the object and the reflection energy of the object is measured at each of the locations. The BRDF of the object can be acquired by expressing a result calculated by measuring all reflection energy to the light sources incident in all the directions by a 4-dimensional function expressed, for example, in the following equation in a polar coordinate system (or spherical coordinate system).

$$f_r(\theta_i, \Phi_i, \theta_r, \Phi_r) = \frac{dL_r(\theta_r, \Phi_r)}{dE_i(\theta_i, \Phi_i)} = \frac{dL_r(\theta_r, \Phi_r)}{L_i(\theta_i, \Phi_i)\cos\theta_i d\omega_r} \quad \text{[Equation 1]}$$

The general BRDF measurement system is constituted by a 4 degree-of-freedom system consisting of two incident angles and two reflection angles. However, this system has a disadvantage of incurring a lot of expenses due to an excessive measurement time of several hours or several tens of hours and massive measurement data in order to acquire information on all direction angles.

SUMMARY OF THE INVENTION

An object of the present invention is to provide a system and a method for measuring reflectance of an object, which can more accurately acquire the reflectance of the object within a shorter time.

In order to achieve the above-mentioned object, a system for measuring reflectance of an object according to an aspect of the present invention includes: a light source unit including a light source irradiating light to the object; a light source position adjusting unit that adjusts a position and a direction of the light source unit; a light receiving unit that acquires image data by detecting light reflected on the object; and a reflectance acquiring unit that acquires the reflectance of the object from the image data.

Herein, the reflectance acquiring unit may acquire the reflectance of the object from the image data by using a correlation between a previously acquired video sensor and a spectral radiation luminance meter at the position of the video sensor.

Herein, the correlation may be acquired by setting a color chart at the position of the object, acquiring the image data by detecting the light reflected on the color chart in the video sensor, acquiring a luminance value by detecting the light reflected on the color chart in the spectral radiation luminance meter, and comparing the image data with the luminance value for each of R, G, and B channels.

Further, the object may have a spherical shape and an isotropic property.

In addition, the light source position adjusting unit may continuously move the position of the light source unit.

Besides, the light receiving unit may acquire the image data at a predetermined interval while the position of the light source unit is continuously changed.

Further, the light source unit may further include a reflecting mirror provided opposite to the object from the light source, a diffuser provided at the side of the object from the light source, a first lens, an iris, and a second lens.

In addition, the light receiving unit may acquire the image data for each wavelength band by filtering the light reflected on the object for each predetermined wavelength band.

Herein, the light receiving unit may include: a liquid crystal tunable filter that filters the light reflected on the object for each predetermined wavelength band; and a video sensor that acquires the image data by detecting the light passing through the liquid crystal tunable filter.

Further, the light source unit may further include a reflecting mirror provided opposite to the object from the light source, a first iris provided at the side of the object from the light source, a first lens, a diffuser, a second lens, and a second iris.

Besides, the reflectance acquiring unit may acquire the reflectance of the object from the image data by using the correlation between the previously acquired video sensor for each wavelength band and the spectral radiation luminance meter at the position of the video sensor.

Herein, the correlation may be acquired by setting the color chart at the position of the object, acquiring the image data by detecting the light reflected on the color chart in the video sensor for each wavelength band, acquiring the luminance value by detecting the light reflected on the color chart in the spectral radiation luminance meter, and comparing the image data with the luminance value for each wavelength band.

In order to achieve the above-mentioned object, a method for measuring reflection of an object according to a second aspect of the present invention includes: acquiring a-correlation between a video sensor and a spectral radiation luminance meter at the same position; irradiating light to the object; acquiring image data by detecting the light reflected on the object with the video sensor; and acquiring the reflectance of the object from the image data by using the correlation.

Herein, acquiring the correlation may include: setting a color chart at the position of a light source; acquiring the image data by detecting the light reflected on the color chart in the video sensor; acquiring a luminance value by detecting the light reflected on the color chart in the spectral radiation luminance meter; and acquiring the correlation by comparing the image data with the luminance value.

Herein, in acquiring the correlation, the correlation may be acquired for each of R, G, and B channels by comparing the image data with the luminance value for each R, G, and B channels.

Alternatively, acquiring the correlation may include: setting the color chart at the position of the light source; acquiring the image data by detecting the light reflected on the color chart in the video sensor for each predetermined wavelength band; acquiring the luminance value by detecting the light reflected on the color chart in the spectral radiation luminance meter; and acquiring the correlation by comparing the image data with the luminance value for each wavelength band.

Alternatively, acquiring the correlation may include: setting a transmissive color chart at the position of the light source; acquiring the image data by detecting the light penetrating the color chart in the video sensor for each predetermined wavelength band; acquiring the luminance value by detecting the light penetrating the color chart in the spectral radiation luminance meter; and acquiring the correlation by comparing the image data with the luminance value for each wavelength band.

Alternatively, in acquiring the image data, the image data may be acquired for each wavelength band by filtering the light reflected on the object for each predetermined wavelength band.

Further, in acquiring the image data, the image data may be acquired at a predetermined interval while the position of the light source irradiating the light is continuously changed.

According to an embodiment of the present invention, it is possible to more accurately acquire reflectance of an object within a shorter time.

DETAILED DESCRIPTION OF THE PREFERRED EMBODIMENTS

Hereinafter, preferred embodiments of the present invention will be described in detail with reference to the accompanying drawings. In the following description and drawings, like components refer to like reference numerals and therefore, the duplicated description thereof will be omitted. In addition, the detailed description of known functions and configurations will be omitted so as not to obscure the subject of the present invention with unnecessary detail.

Figure 1:
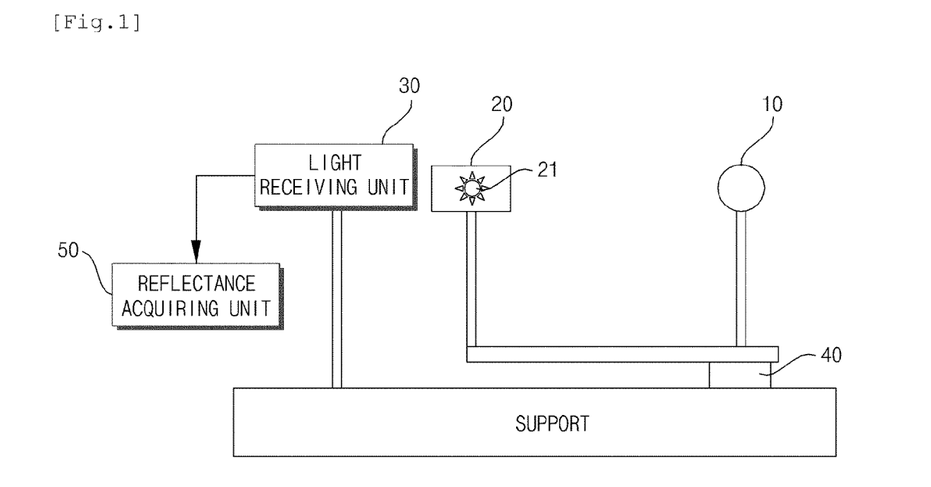
FIG. 1 is a diagram illustrating a configuration of a system for measuring reflectance of an object according to an embodiment of the present invention.

FIG. 1 is a diagram illustrating a configuration of a system for measuring reflectance of an object according to an embodiment of the present invention. Referring to FIG. 1, the reflectance measuring system according to the embodiment of the present invention includes an object 10 which is a target of measuring the reflectance, a light source unit 20 including a light source 21 irradiating light to the object 10, a light receiving unit 30 that detects light reflected from the object 10 to acquire image data, a light source position adjusting unit 40 that adjusts a position and a direction of the light source unit 20, and a reflectance acquiring unit 50 that acquires the reflectance of the object 10 by using the image data acquired in the light receiving unit 30. In addition, although not shown, the reflectance measuring system according to the embodiment of the present invention may further include an object position adjusting unit that adjusts a position of the object 10.

The object 10 has a spherical shape and an isotropic property. The light source unit 20 transforms the light emitted from the light source 21 to light having uniformity and straightness and irradiates the light to the object 10. The light source position adjusting unit 40 rotates the light source unit 21 around the object 10 to adjust the position and direction of the light source unit 21. The light source position adjusting unit 40 continuously moves the position of the light source unit 21 without stopping the position of the light source unit 21 and the light receiving unit 30 acquires the image data at a predetermined interval while the position of the light source unit 21 is continuously changed.

In the first embodiment of the present invention, the video sensor may be used as the light receiving unit 30 and since the video sensor detects light in a wider area than a general CCD sensor to acquire the image data, the video sensor can acquire the reflectance without stopping the light source 21 every time. Further, the video sensor can acquire a precision BRDF by making an interval of acquiring the image data dense. A high dynamic range (HDR) camera may be adopted as the video sensor and it is possible to acquire a more accurate measurement value by installing a high-magnification lens in front of the video sensor to increase resolution.

Figure 2:
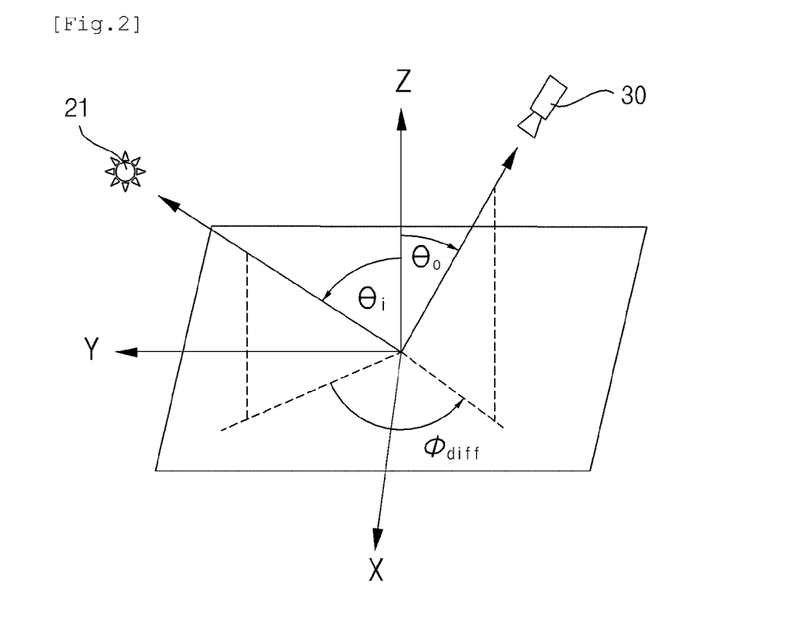
FIG. 2 is a diagram illustrating a reflection relationship relating to reflectance of an object.

FIG. 2 is a diagram illustrating a reflection relationship relating to reflectance of an object. Referring to FIG. 2, the light irradiated from the light source 21 is reflected on the object 10 to be measured and detected by the light receiving unit 30 and since the object 10 has the isotropic property, a reflection characteristic is not changed in spite of rotating an incidence surface and a reflection surface at once on the basis of a normal vector of one point on the surface of the object 10 regardless of the direction of the light, the reflectance can be expressed as an isotropic BRDF. That is, as shown in FIG. 2, since the reflection characteristic is not changed in spite of rotating the object around the normal vector Z, the reflectance can be expressed as a 3-dimensional function described by a ratio of energy $E_i$ of incident light and energy $L_r$ of reflected light as shown in the following equation.

$$f_r(\theta_i, \theta_r, \phi_{diff}) = \frac{dL_r(\theta_r, \phi_{diff})}{dE_i(\theta_i, \phi_{diff})} = \frac{dL_r(\theta_r, \phi_{diff})}{L_i(\theta_i, \phi_{diff})\cos\theta_i d\omega_r} \quad \text{[Equation 2]}$$

Herein, $\theta_i$ represents a vertical angle for a normal vector of incident light, $\theta_r$ represents a vertical angle for a normal vector of reflected light, and $\phi_{diff}$ represents a difference of a projection angle to a tangent plane of the incident light and the reflected light. In general, in order to measure a 3-dimensional isotropic BRDF, a 3 degree-of-freedom measurement system is required, but when the object 10 has the spherical shape as described in the embodiment of the present, the system may be simplified into a 1 degree-of-freedom measurement system. As described in FIG. 1, it is possible to acquire the BRDF using a fixed light receiving unit 30 only by rotating the light source unit 21 around the object 10.

Figure 3:
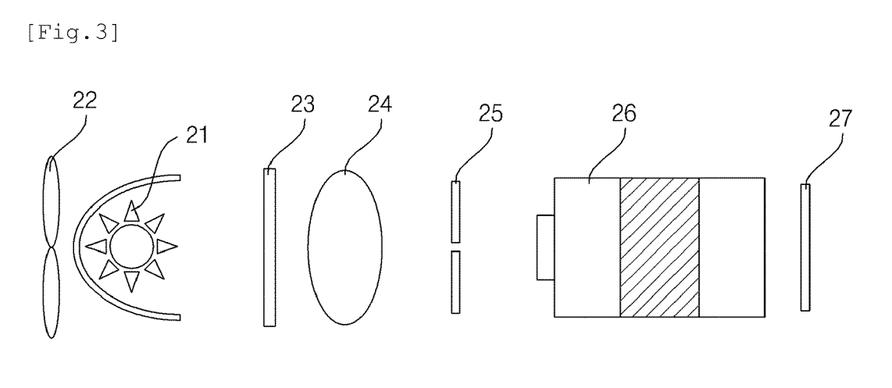
FIG. 3 illustrates a first embodiment of a light source unit 20 in detail.

FIG. 3 illustrates a first embodiment of a light source unit 20 in detail. In order to accurately and densely measure the reflectance, the light should be uniformly irradiated in a predetermined area and it is preferable that the characteristic of the light is not changed as time elapses. In addition, according to the embodiment of the present invention, since the light receiving unit 30 detects light in a wide area by using the video sensor, the light should be irradiated in parallel in a predetermined area. In addition, it is preferable that the irradiated light is bright and has a wavelength of approximately 300 nm to 800 nm which is a visible-ray region.

Referring to FIG. 3, the light source unit 20 according to the embodiment of the present invention includes a cooler 22 that cools heat generated from the light source 21 opposite to the object 10 from the light source 21. For example, a fan may be adopted as the cooler 22 as shown in the figure. In addition, a reflecting mirror 21 is installed opposite to the object 10 from the light source 21 to increase the efficiency of the light. Further, at the side of the object 10 from the light source 21, there are provided a diffuser 23 for removing undesired light, a first lens 24 (i.e., aspheric condenser lens) for making a point light source by focusing the light, an iris 25 for shielding light acting as noise, a second lens 26 (i.e., camera lens) for transforming the light to parallel light, and a filter 27 (i.e., color temperature filter or ND filter) for changing light characteristics such as color temperature, quantity of light, etc. If the light source unit 20 is configured as above, it is possible to generate light having unchanged light characteristics, uniformity, and parallelism as time elapses in a predetermined area.

In order to acquire the reflectance of the object 10 from the image data acquired by the light receiving unit 30, calibration of the video sensor of the light receiving unit 30 is previously required.

Figure 4:
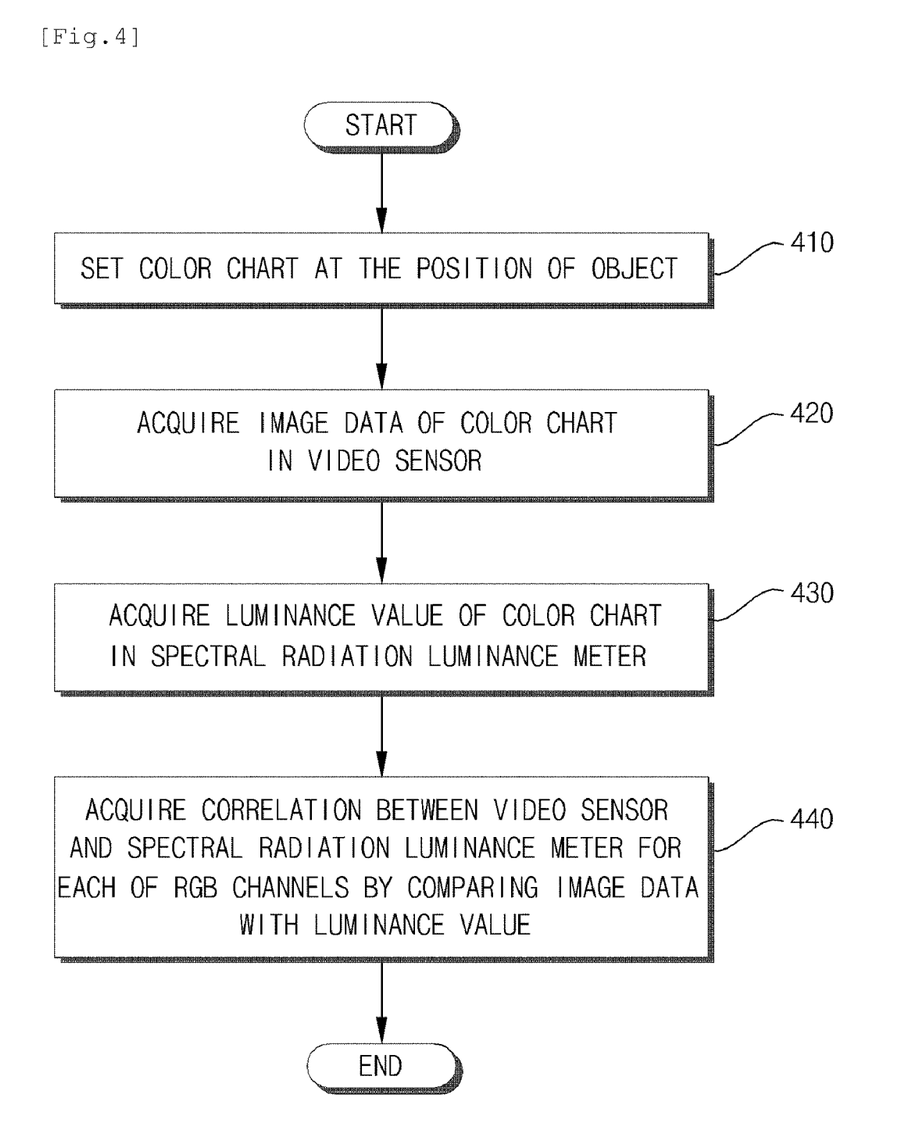
FIG. 4 is a flowchart illustrating a process of performing calibration of a video sensor of a light receiving unit 30 according to a first embodiment of the present invention.

FIG. 4 is a flowchart illustrating a process of performing calibration of a video sensor of a light receiving unit 30 according to a first embodiment of the present invention.

Figure 5:
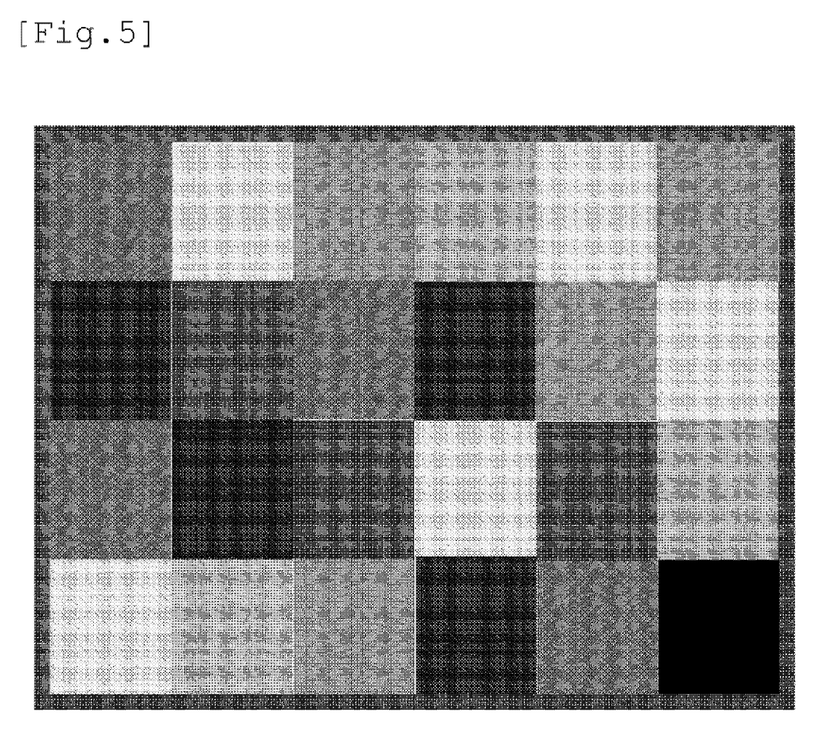
FIG. 5 illustrates a Gretag Macbeth color chart as an example of a color chart used in a first embodiment of the present invention.

First, the light source 21 is positioned at a predetermined location and a color chart having a predetermined color pattern is set at the position of the object 10 instead of the object 10 (S410). FIG. 5 illustrates a Gretag Macbeth color chart as an example of a color chart used in the embodiment of the present invention.

In addition, the image data of the color chart is acquired by detecting the light reflected on the color chart with the video sensor of the light receiving unit 30 (S420). Next, a spectral radiation luminance meter is installed at the position of the video sensor of the light receiving unit 30 instead of the video sensor and luminance and chromaticity of the color chart are acquired by detecting the light reflected on the color chart with the spectral radiation luminance meter (S430). At this time, the luminance and chromaticity are acquired for each color sample provided by the color chart with the spectral radiation luminance meter. In addition, a correlation between the video sensor and the spectral radiation luminance meter is acquired for each of the R, G, and B channels by comparing the image data acquired by the video sensor of the light receiving unit 30 and the luminance acquired by the spectral radiation luminance meter (S440). S440 will be described in more detail below.

In the video sensor, a value of each pixel for each of the R, G, and B channels is acquired and in the spectral radiation luminance meter, spectral distribution of the light is acquired. The spectral distribution of the light is transformed to a CIE XYZ value which is a tristimulus value by using a well-known color transformation formula and the CIE XYZ value can be transformed to R, G, B values by using the well-known color transformation formula. In order to acquire a more accurate correlation, several measurements are performed, for example, two values are compared with each other by using a least square fitting technique to acquire the correlation between the video sensor and the spectral radiation luminance meter.

Figure 6:
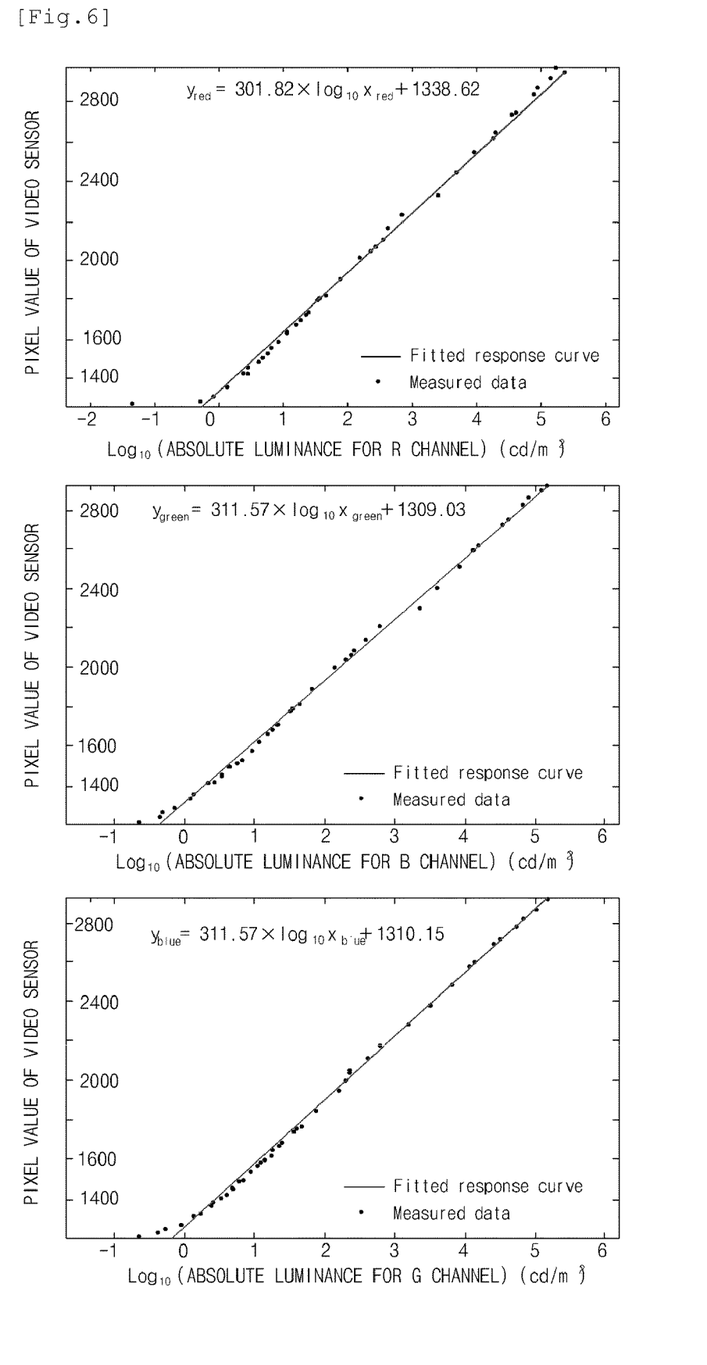
FIG. 6 is a graph illustrating an example of a result of fitting a video sensor and a spectral radiation luminance meter as a result of performing calibration of the video sensor of a light receiving unit 30 according to a first embodiment of the present invention.

FIG. 6 is a graph illustrating an example of a result of fitting a video sensor and a spectral radiation luminance meter as a result of performing calibration of the video sensor of a light receiving unit 30 according to a first embodiment of the present invention. Since the color channels are different from each other, absolute calibration of the video sensor is separately determined for each of the R, G, and B channels. The spectral radiation luminance meter provides the luminance (Y) and chromaticity (x,y) of each color sample. The values are transformed to CIE XYZ which is the tristimulus value. The XYZ values can be transformed to absolute values of RGB by using an sRGB transformation matrix. Therefore, output values of the video sensor can be fitted to luminance and chromaticity values. For example, as shown in the figure, parameters a and b of a logarithmic function $y_i = a*\log_{10}(x_i) + b$ are determined for each of the R, G, and B channels by using the least square fitting technique. As shown in the figure, an absolute response curve for each of the R, G, and B channels can be determined by using the logarithmic function.

In the first embodiment of the present invention, the reflectance acquiring unit 50 acquires the BRDF by using the correlation between the video sensor and the spectral radiation luminance meter of the light receiving unit 30, which acquired as above with the image data acquired by detecting the light reflected on the object 10. The pixel value is acquired for each of the R, G, and B channels from the image data acquired by the video sensor and the BRDF value can be acquired from the pixel values for each of the R, G, and B channel by using a relational expression generated from the correlation between the video sensor and the spectral radiation luminance meter. For example, when R, G, and B values of one pixel in the image data acquired by the video sensor are 2000, 1876, and 2530, values transformed from the values by using a function obtained through the correlation are 198, 174, and 254. The transformed values are absolute values having a unit of cd/m2. That is, the image data acquired by the video sensor has a pixel value for each pixel and each pixel value is transformed to the absolute value by using the function obtained through the correlation. According to the embodiment, since the correlation between the video sensor and the spectral radiation luminance meter is used, it is possible to acquire the absolute BRDF value.

In the second embodiment of the present invention, as the object 10, an object that is coated with pearlescent pigment, has a spherical shape, and an isotropic property may be used.

The pearlescent pigment commonly designates pigments expressing a pearlised color, a rainbow color, and a metallic color. Particles of the pearlescent pigment have a transparent and thin flake shape of a high refractive index. The pearlescent pigment has the dual or multiple pearlised colors due to an interference effect of the light. The pearlescent pigment is widely used as an exterior material additive of various industrial products such as automobiles, cosmetics, plastics, etc. with a gentrified tendency of a design.

When the pearlescent pigment is added, the pearlised color is expressed due to a difference in an angle generated when some of light passing through a pigment layer is reflected and the other is refracted. In other words, a substrate such as mica is coated with metal oxides having the high refractive index or a mixture thereof in a single layer or multi-layers, such that a contact surface between two layers having different refractive indexes allows the visible rays to be partially refracted and transmitted. At this time, the visible rays reflected or transmitted on the contact surface are intensified or attenuated, such that the intensity is increased only for a predetermined wavelength. As a result, a color corresponding to a wavelength intensified at a predetermined reflection angle is observed.

The pearlescent effect is widely used in industrial fields with the gentrified tendency of the design, a research necessity is being increased. In particular, the pearlescent effect has been actively researched in a computer-aided design (CAD) field, a computer graphics field, and an optical field. In recent years, a measure-and-fit method experimentally verified by Addy Ngan has been primarily used in the computer graphics field, but the known lobe-based BRDF models (Phong, Cook-Torrance, etc.) cannot have an effect (color shift, angle-dependent color, flip-flop, and goniochromatic) in which a color is shifted depending on the incident angle and the reflection angle among the pearlescent effects.

Hereinafter, as the second embodiment of the present invention, a system and a method for measuring reflection of an object that can accurately show a pearlescent effect will be described. The system for measuring the reflectance of the object according to the embodiment has the same configuration as the system shown in FIG. 1, but the embodiment is different from the first embodiment in detailed configurations and operations of the light source unit 20, the light receiving unit 30, and the reflectance acquiring unit 50. According to the first embodiment, since the BRDF is measured for each of the R, G, and B channels, it is difficult to accurately measure the pearlescent effect sensitive to the wavelength. That is, it is difficult to accurately measure an interference effect of the pearlescent pigment of which an optical property is changed depending on the incident angle and the reflection angle by means of the RGB-based measurement system. Accordingly, in the embodiment, it is possible to accurately show the pearlescent effect by measuring the BRDF for each wavelength.

Figure 7:
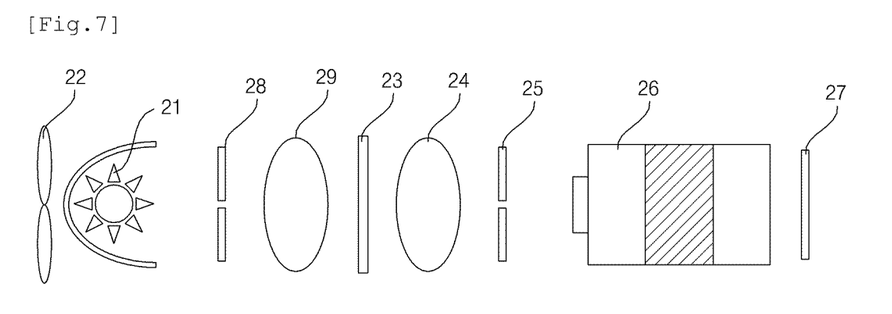
FIG. 7 illustrates a second embodiment of a light source unit 20 in detail.

FIG. 7 illustrates a second embodiment of a light source unit 20 in detail. The light source unit 20 according to the embodiment further includes an iris 28 and an aspheric condenser lens 29 between the light source 21 and the diffuser 23 in comparison with the first embodiment shown in FIG. 3. According to the embodiment, unnecessary light distorted due to polarization is removed by installing the iris 28 in front of the light source unit 21. The light passing through the iris 28 is focused by passing through the aspheric condenser lens 29 and the light still having polarization components passes through the diffuser 23, such that the polarization component thereof is decreased. The light passing through the diffuser 23 passes through the iris 25 again to form the point light source and further passes through the second lens 26 and the filter 27 to head for the object 10.

As described below, the light reflected on the object 10 passes through the liquid crystal tunable filter and since the liquid crystal tunable filter has small spectral transmittance in a predetermined wavelength region, it is possible to use a more intense light source by means of the configuration of the light source unit 20.

Figure 8:
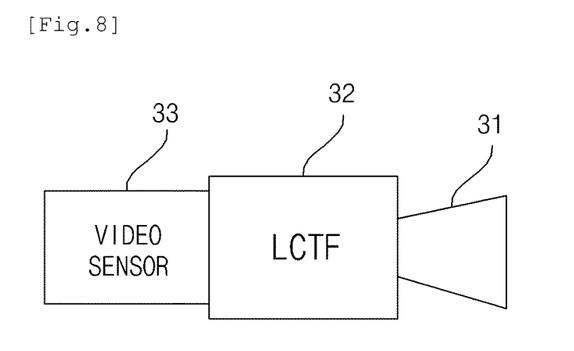
FIG. 8 illustrates a configuration of a light receiving unit 30 according to a second embodiment of the present invention.

FIG. 8 illustrates a configuration of a light receiving unit 30 according to a second embodiment of the present invention. The light receiving unit 30 according to the embodiment of the present invention acquires image data for each wavelength band by filtering the light reflected on the object 10 for each predetermined wavelength band. For this, as shown in the figure, the light receiving unit 30 includes a lens 31, a liquid crystal tunable filter (LCTF) 32 filtering the light reflected on the object, which passes through the lens 31 for each predetermined wavelength band, and a video sensor 33 that detects the light passing through the liquid crystal variable filter 32 to acquire the image data. Like the first embodiment, the high dynamic range (HDR) camera can be adopted as the video sensor 33 and the lens 31 is preferably the high-magnification lens. The liquid crystal tunable filter 32 can tune a wavelength passing band at a high speed depending on user set-up with a wavelength passing band having a size of, for example, 20 nm.

The light receiving unit 30 according to the embodiment of the present invention acquires the image data for each wavelength band by using the liquid crystal tunable filter 32 and the video sensor 33. For example, when the liquid crystal tunable filter 32 is set to sequentially filter the light at an interval of 10 nm in a wavelength passing band having a size of 20 nm through a wavelength range of 400 nm to 720 nm, total thirty one image data will be acquired for each of 400 nm to 420 nm, 410 nm to 430 nm, . . . , 700 nm to 720 nm from the video sensor 33.

Hereinafter, a calibration process of the video sensor 33 of the light receiving unit 30 will be described, which is previously performed in order to acquire the reflectance of the object 10 from the image data for each wavelength band acquired in the light receiving unit 30.

Figure 9:
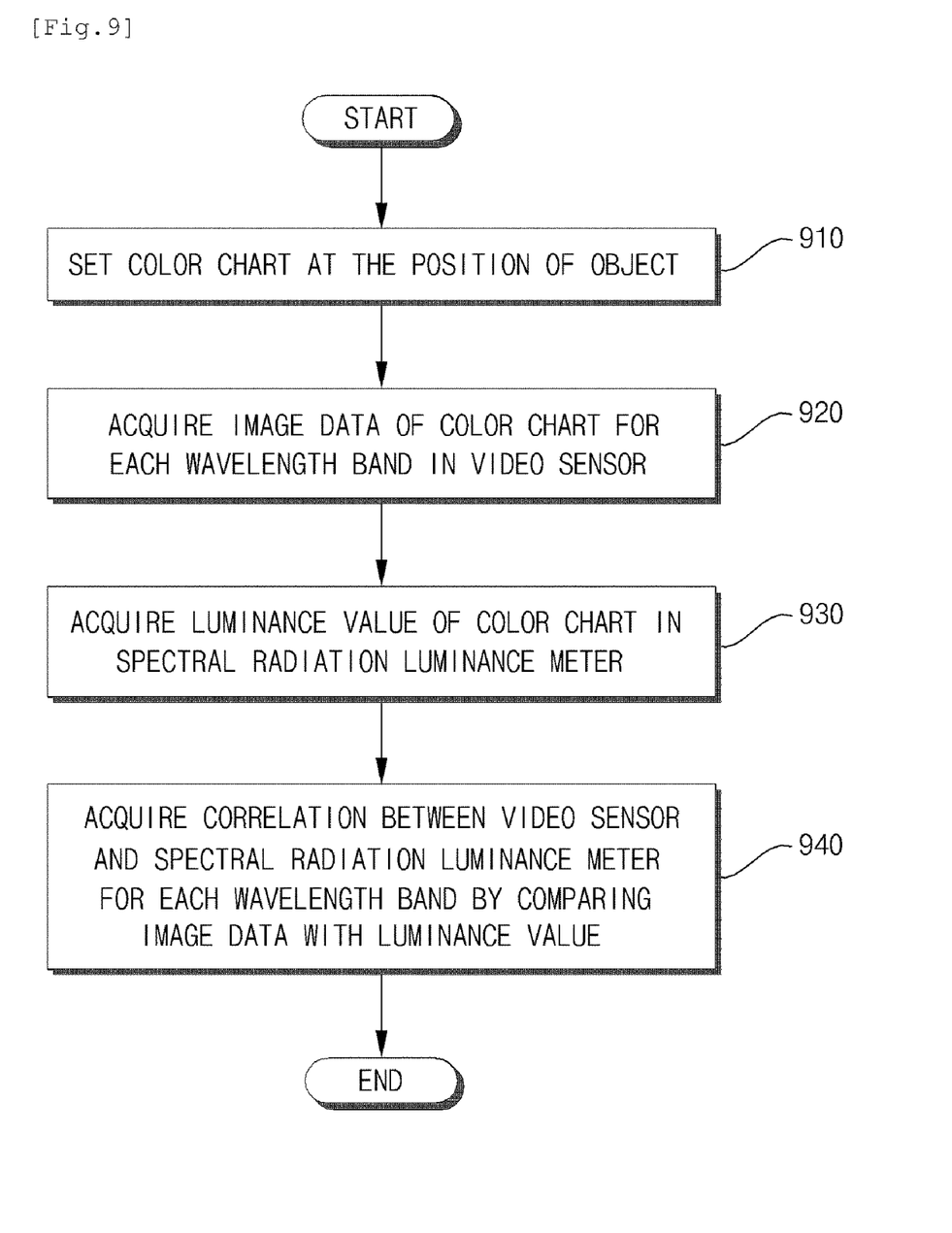
FIG. 9 is a flowchart illustrating a process of performing calibration of a video sensor 33 of a light receiving unit 30 according to a second embodiment of the present invention.

FIG. 9 is a flowchart illustrating a process of performing calibration of a video sensor 33 of a light receiving unit 30 according to a second embodiment of the present invention.

First, the light source 21 is positioned at a predetermined location and the color chart having a predetermined color pattern is set at the position of the object 10 instead of the object 10 (S910). In the embodiment, the Gretag Macbeth color chart shown in FIG. 5 can also be used.

Figure 10:
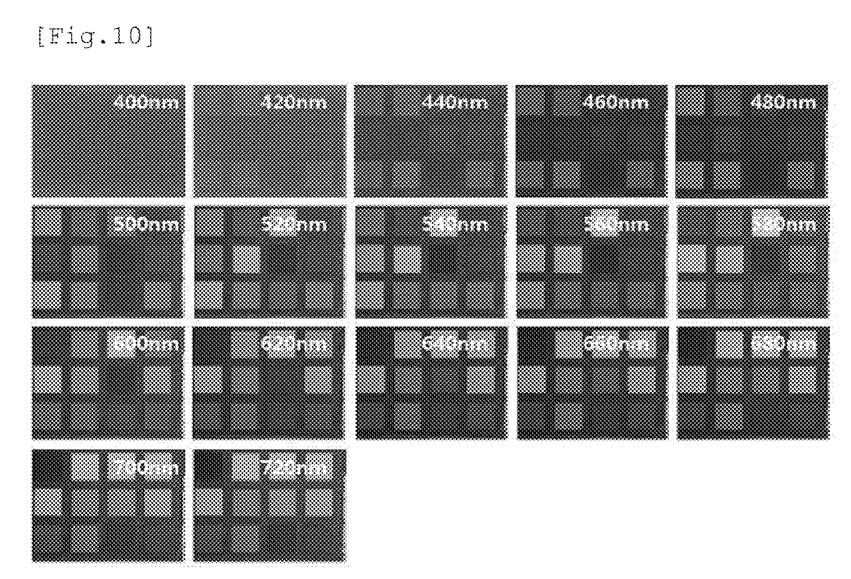
FIG. 10 illustrates examples of images of color charts acquired for each wavelength band in a video sensor 33.

In addition, the image data of the color chart is acquired for each wavelength band by detecting the light reflected on the color chart by using the liquid crystal tunable filter 32 and the video sensor 33 of the light receiving unit 30 (S920). FIG. 10 illustrates examples of images of color charts acquired for each wavelength band in a video sensor 33.

Next, the spectral radiation luminance meter is installed at the position of the light receiving unit 30 and the luminance and chromaticity of the color chart are acquired by detecting the light reflected on the color chart with the spectral radiation luminance meter (S930). Further, a correlation between the video sensor 33 and the spectral radiation luminance meter is acquired for each wavelength band by comparing the image data for each wavelength band acquired by the video sensor 33 of the light receiving unit 30 and the luminance acquired by the spectral radiation luminance meter (S940). S940 will be described in more detail below.

According to the embodiment, since the light filtered for each wavelength band by using the liquid crystal tunable filter 32 is detected in the video sensor 33, the pixel value is acquired for each wavelength band. In addition, the spectral distribution of the light is acquired in the spectral radiation luminance meter. Accordingly, unlike the first embodiment, in the embodiment, the spectral distribution of the light acquired in the spectral radiation luminance meter does not need to be transformed to R, G, and B values and the correlation can be directly acquired with the pixel value acquired in the video sensor 33 and the luminance acquired in the spectral radiation luminance meter. At this time, like the first embodiment, the correlation between the video sensor 33 and the spectral radiation luminance meter can be acquired by using the least square fitting technique after several measurements.

Figure 11:
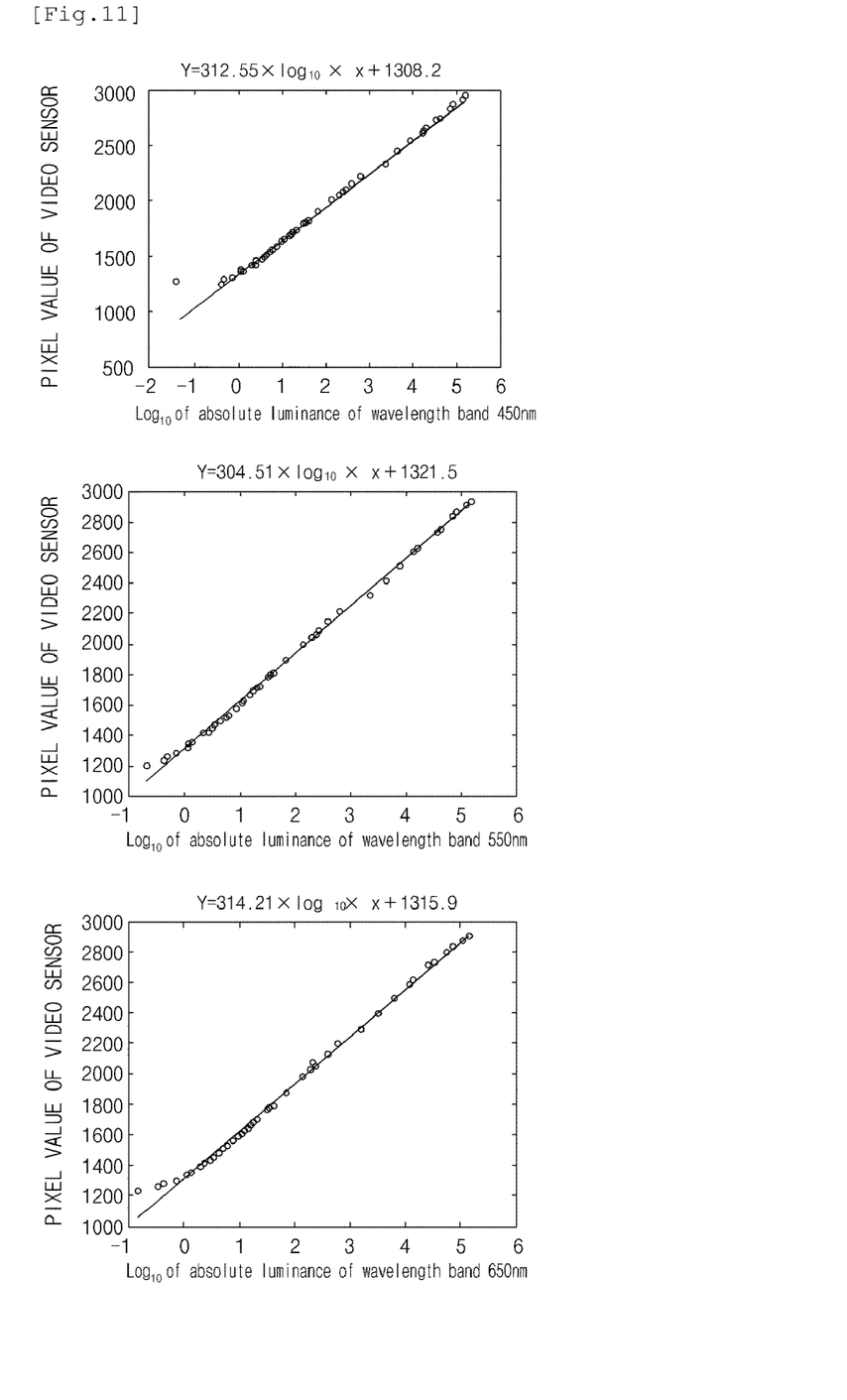
FIG. 11 illustrates an example of a result of fitting a video sensor 33 and a spectral radiation luminance meter for each wavelength band as a result of performing calibration of the video sensor 33 of a light receiving unit 30 according to a second embodiment of the present invention.

FIG. 11 illustrates an example of the result of fitting the video sensor 33 and the spectral radiation luminance meter for each wavelength band as the result of performing calibration of the video sensor 33 of the light receiving unit 30 according to the second embodiment of the present invention. In FIG. 11, three cases in which central wavelengths of the wavelength band are 450 nm, 550 nm, and 650 nm are exemplified. As shown in the figure, parameters a and b of a logarithmic function $y=a*\log_{10}(x)+b$ are determined for each of the R, G, and B channels by using the least square fitting technique. The absolute response curve can be determined for each wavelength band by using the logarithmic function.

In the second embodiment of the present invention, the reflectance acquiring unit 50 acquires the BRDF by using the correlation between the video sensor 33 and the spectral radiation luminance meter for each wavelength band, which acquired as above with the image data for each wavelength band acquired in the light receiving unit 30 by detecting the light reflected on the object 10. The pixel value for each wavelength band is acquired from the image data for each wavelength band acquired by using the liquid crystal tunable filter 32 and the video sensor 33 and the BRDF value for each wavelength band can be acquired by using the relational expression generated from the correlation between the video sensor 33 and the spectral radiation luminance meter from the pixel values.

As a modified example of the calibration of the video sensor 33 of the light receiving unit 30 according to the second embodiment, the video sensor 33 and the spectral radiation luminance meter may acquire the light that is emitted from the light source and penetrates the color chart without acquiring the light that is emitted from the light source and reflected on the color chart. In this case, as the color chart, a transmissive color chart (ESSER Imaging Engineering) shown in FIG. 12 can be used instead of the Gretag Macbeth color chart.

Even though an intensive light source is used in the light source unit 20, the spectral transmittance of the liquid crystal tunable filter 32 is small in a predetermined wavelength region, such that the intensity of the light detected in the video sensor 33 may be small. In the case of the reflective color chart, the light is dispersed due to reflection, such that only some of the light is inputted into the liquid crystal tunable filter 32. Therefore, in the embodiment, the light emitted from the light source penetrates the color charts to be irradiated directly to the liquid crystal tunable filter 32 by using the transmissive color chart instead of the reflective color chart. As such, it is possible to increase the intensity of the light detected in the video sensor 33 by using the transmissive color chart. However, in order to use the transmissive color chart, the light source unit 20 of FIG. 1 should be positioned opposite to the light receiving unit 30 on the basis of the object 10.

In order to express the image data for each wavelength band acquired in the video sensor 33, spectral radiation $I_R(\lambda)$ of the light source, spectral reflectivity $r(\lambda)$ of the object 10, spectral transmittance $o(\lambda)$ of the lens 31, spectral reflectance $\phi_k(\lambda)$ of the liquid crystal tunable filter 32, and spectral sensitivity $a(\lambda)$ of the video sensor 33 should be considered. Elements that should be considered as important among them are the spectral radiation of the light source, the spectral transmittance of the liquid crystal tunable filter 32, and the spectral sensitivity of the video sensor 33. CIE XYZ values acquired by the parameters are as follows.

$$X = k \int_{380}^{780} I_R(\lambda)r(\lambda)o(\lambda)\phi_k(\lambda)a(\lambda)x(\lambda)d\lambda \quad \text{[Equation 3]}$$

$$Y = k \int_{380}^{780} I_R(\lambda)r(\lambda)o(\lambda)\phi_k(\lambda)a(\lambda)y(\lambda)d\lambda$$

$$Z = k \int_{380}^{780} I_R(\lambda)r(\lambda)o(\lambda)\phi_k(\lambda)a(\lambda)z(\lambda)d\lambda$$

Herein, $x(\lambda)$, $y(\lambda)$, and $z(\lambda)$ are color matching functions and k is a normalization constant.

Figure 13:
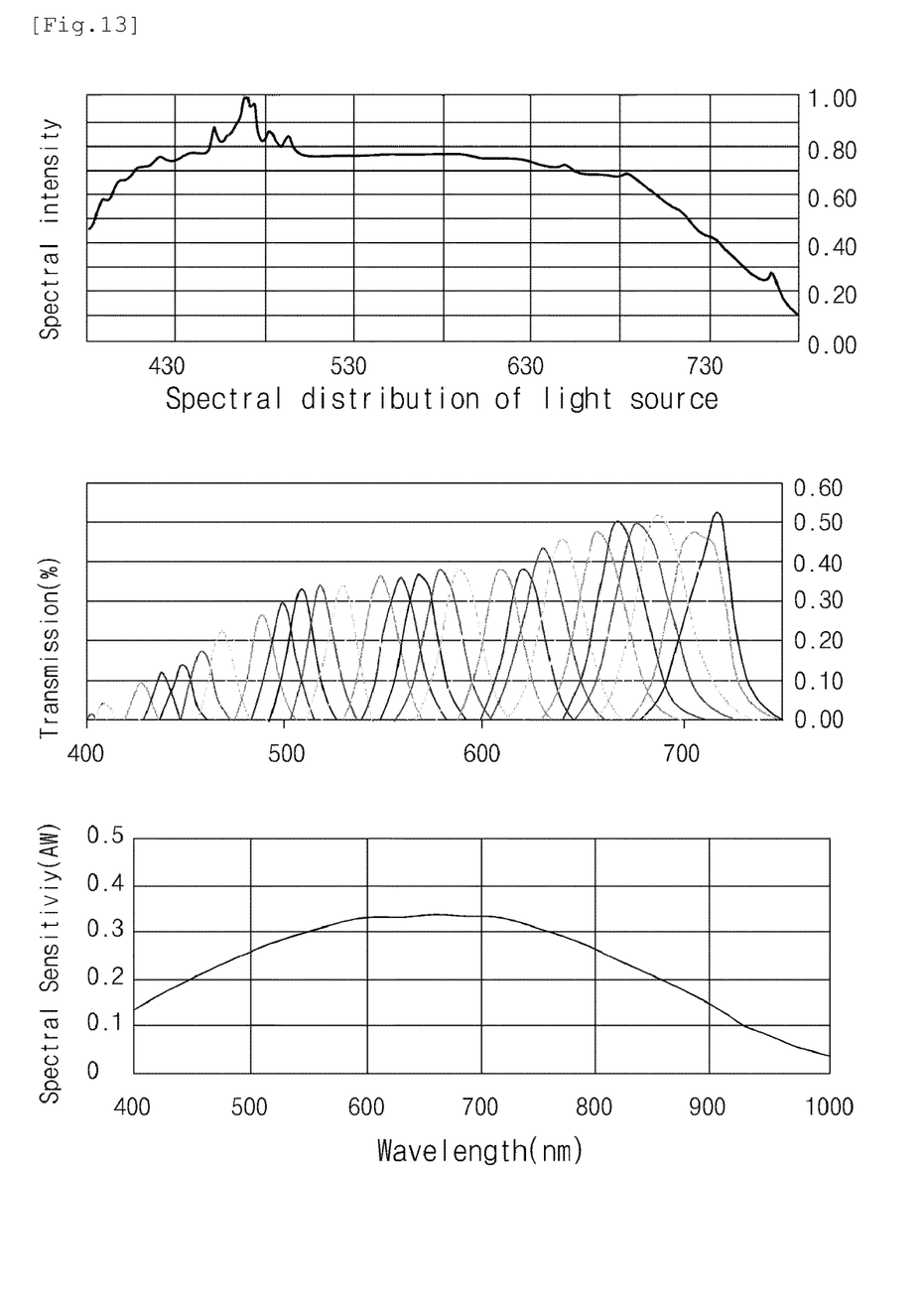
FIG. 13 is a graph illustrating spectral radiation of a light source, spectral transmittance of a liquid crystal tunable filter 32, and spectral sensitivity of a video sensor 33.

FIG. 13 is a graph illustrating the spectral radiation of the light source, the spectral transmittance of the liquid crystal tunable filter 32, and the spectral sensitivity of the video sensor 33 sequentially from the above. Referring to FIG. 13, they do not show a uniform property depending on the wavelength. For example, the spectral transmittance of the liquid crystal tunable filter 32 increases as the wavelength increases, such that compensation should be performed for each wavelength. The spectral sensitivity of the video sensor 33 increases up to approximately 600 nm, but decreases from 700 nm. As such, the spectral sensitivity of the video sensor 33 shows a non-uniform property for each wavelength band. Therefore, in the embodiment, the CIE XYZ values are acquired by compensating the spectral radiation of the light source, the spectral transmittance of the liquid crystal tunable filter 32, and the spectral sensitivity of the video sensor 33.

Figure 12:
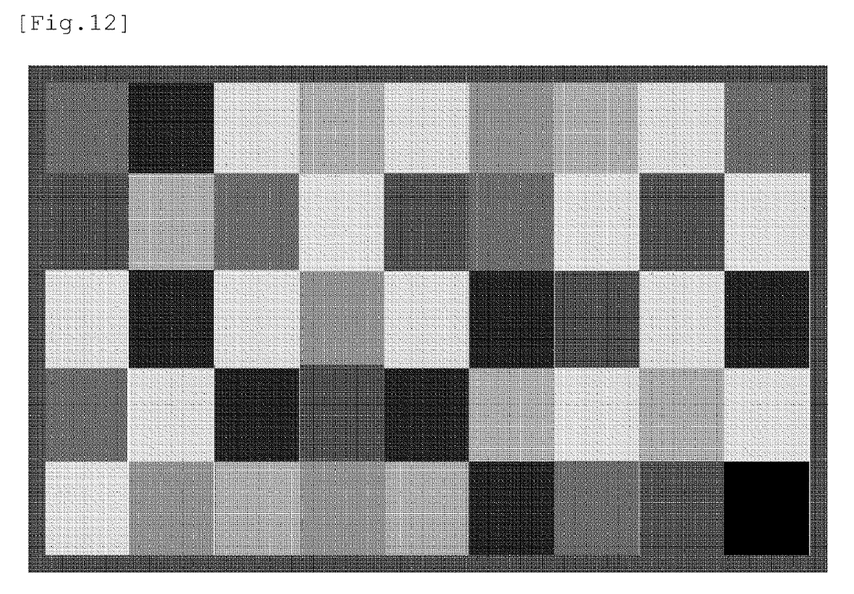
FIG. 12 illustrates a transmissive color chart used in a modified example of a second embodiment of the present invention.

Since characteristics for each wavelength band of the light source, the liquid crystal tunable filter 32, and the video sensor 33 can be previously known as shown in FIG. 12, a compensation coefficient for compensating the characteristic for each wavelength band can be acquired on the basis of the characteristics. Assuming that the compensation coefficient of the light source, the compensation coefficient of the liquid crystal tunable filter 32, and the compensation coefficient of the video sensor 33 are $\alpha(\lambda)$, $\beta(\lambda)$, and $\gamma(\lambda)$, respectively, Equation 3 is modified as follows.

$$X = k \int_{380}^{780} \alpha(\lambda)I_R(\lambda)r(\lambda)o(\lambda)\beta(\lambda)\phi_K(\lambda)\gamma(\lambda)a(\lambda)x(\lambda)d\lambda \quad \text{[Equation 4]}$$

$$Y = k \int_{380}^{780} \alpha(\lambda)I_R(\lambda)r(\lambda)o(\lambda)\beta(\lambda)\phi_K(\lambda)\gamma(\lambda)a(\lambda)y(\lambda)d\lambda$$

$$Z = k \int_{380}^{780} \alpha(\lambda)I_R(\lambda)r(\lambda)o(\lambda)\beta(\lambda)\phi_K(\lambda)\gamma(\lambda)a(\lambda)z(\lambda)d\lambda$$

However, Equation 4 corresponds to a case in which a spectrum is continuous. In the embodiment, since the liquid crystal tunable filter 32 is a device having a variable wavelength band, an actually used equation is as follows.

$$X = k \sum_{400}^{720} \alpha_\lambda I_{R,\lambda} r_\lambda o_\lambda \beta_\lambda \phi_{K,\lambda} \gamma_\lambda a_\lambda x_\lambda \Delta\lambda \quad \text{[Equation 5]}$$

$$Y = k \sum_{400}^{720} \alpha_\lambda I_{R,\lambda} r_\lambda o_\lambda \beta_\lambda \phi_{K,\lambda} \gamma_\lambda a_\lambda y_\lambda \Delta\lambda$$

$$Z = k \sum_{400}^{720} \alpha_\lambda I_{R,\lambda} r_\lambda o_\lambda \beta_\lambda \phi_{K,\lambda} \gamma_\lambda a_\lambda z_\lambda \Delta\lambda$$

Up to now, the preferred embodiments of the present invention have been described. It will be appreciated by those skilled in the art that various modifications and changes can be made without departing from the spirits and scope of the appended claims of the present invention. Therefore, the disclosed embodiments should be considered not from a limitative aspect but from a descriptive aspect. The scope of the present invention is shown not in the above description but the appended claims. It will be appreciated that all differences within the ranges equivalent thereto are included in the present invention.

What is claimed is:

1. A system for measuring reflectance of an object, comprising:
    a light source unit including a light source irradiating light to the object;
    a light source position adjusting unit that adjusts a position and a direction of the light source unit;
    a light receiving unit that acquires image data by detecting light reflected on the object; and
    a reflectance acquiring unit that acquires the reflectance of the object from the image data,
    wherein the reflectance acquiring unit acquires the reflectance of the object from the image data by using a correlation between a previously acquired video sensor and a spectral radiation luminance meter at the position of the video sensor, and
    wherein the correlation is acquired by setting a color chart at the position of the object, acquiring the image data by detecting the light reflected on the color chart in the video sensor, acquiring a luminance value by detecting the light reflected on the color chart in the spectral radiation luminance meter, and comparing the image data with the luminance value for each of R, G, and B channels.

2. The system for measuring reflectance of an object according to claim 1, wherein the object has a spherical shape and an isotropic property.

3. The system for measuring reflectance of an object according to claim 1, wherein the light source position adjusting unit continuously moves the position of the light source unit.

4. The system for measuring reflectance of an object according to claim 3, wherein the light receiving unit acquires the image data at a predetermined interval while the position of the light source unit is continuously changed.

5. The system for measuring reflectance of an object according to claim 1, wherein the light source unit further includes a reflecting mirror provided opposite to the object from the light source, a diffuser provided at the side of the object from the light source, a first lens, an iris, and a second lens.

6. The system for measuring reflectance of an object according to claim 1, wherein the light receiving unit acquires the image data for each wavelength band by filtering the light reflected on the object for each predetermined wavelength band.

7. The system for measuring reflectance of an object according to claim 6, wherein the light receiving unit includes:
    a liquid crystal tunable filter that filters the light reflected on the object for each predetermined wavelength band; and
    a video sensor that acquires the image data by detecting the light passing through the liquid crystal tunable filter.

8. The system for measuring reflectance of an object according to claim 6, wherein the light source unit further includes a reflecting mirror provided opposite to the object from the light source, a first iris provided at the side of the object from the light source, an first lens, a diffuser, a second lens, and a second iris.

9. The system for measuring reflectance of an object according to claim 6, wherein the reflectance acquiring unit acquires the reflectance of the object from the image data by using the correlation between the previously acquired the video sensor for each wavelength band and the spectral radiation luminance meter at the position of the video sensor.

10. The system for measuring reflectance of an object according to claim 1, wherein the correlation is acquired by setting the color chart at the position of the object for each wavelength band, acquiring the image data by detecting the light reflected on the color chart in the video sensor, acquiring the luminance value by detecting the light reflected on the color chart in the spectral radiation luminance meter, and comparing the image data with the luminance value for each wavelength band.

11. A method for measuring reflectance of an object, comprising:
    acquiring a correlation between a video sensor and a spectral radiation luminance meter at the same position;
    irradiating light to the object;
    acquiring image data by detecting the light reflected on the object with the video sensor; and
    acquiring the reflectance of the object from the image data by using the correlation, wherein acquiring the correlation includes:
    setting a color chart at the position of a light source;
    acquiring the image data by detecting the light reflected on the color chart in the video sensor;
    acquiring a luminance value by detecting the light reflected on the color chart in the spectral radiation luminance meter; and
    acquiring the correlation by comparing the image data with the luminance value.

12. The method for measuring reflectance of an object according to claim 11, wherein in acquiring the correlation, the correlation is acquired for each of R, G, and B channels by comparing the image data with the luminance value for each of the R, G, and B channels.

13. The method for measuring reflectance of an object according to claim 11, wherein acquiring the correlation includes:
    setting the color chart at the position of the light source;
    acquiring the image data by detecting the light reflected on the color chart in the video sensor for each predetermined wavelength band;
    acquiring the luminance value by detecting the light reflected on the color chart in the spectral radiation luminance meter; and
    acquiring the correlation by comparing the image data with the luminance value for each wavelength band.

14. The method for measuring reflectance of an object according to claim 11, wherein in acquiring the image data, the image data is acquired for each wavelength band by filtering the light reflected on the object for each predetermined wavelength band.

15. The method for measuring reflectance of an object according to claim 11, wherein in acquiring the image data, the image data is acquired at a predetermined interval while the position of the light source irradiating the light is continuously changed.

16. A method for measuring reflectance of an object, comprising:
    acquiring a correlation between a video sensor and a spectral radiation luminance meter at the same position;
    irradiating light to the object;
    acquiring image data by detecting the light reflected on the object with the video sensor; and
    acquiring the reflectance of the object from the image data by using the correlation, wherein acquiring the correlation includes:
    setting a transmissive color chart at the position of the light source;
    acquiring the image data by detecting the light penetrating the color chart in the video sensor for each predetermined wavelength band;
    acquiring the luminance value by detecting the light penetrating the color chart in the spectral radiation luminance meter; and
    acquiring the correlation by comparing the image data with the luminance value for each wavelength band.

\* \* \* \* \*